(12) United States Patent
Dao et al.

(10) Patent No.: US 8,465,731 B2
(45) Date of Patent: Jun. 18, 2013

(54) PROBIOTIC COLOR COSMETIC COMPOSITIONS AND METHODS

(75) Inventors: Khanh Ngoc Dao, Ronkonkoma, NY (US); Clara G. Mercado, Saddle River, NJ (US); John F. Logalbo, Dix Hills, NY (US)

(73) Assignee: ELC management, LLC, New York, NY (US)

( * ) Notice: Subject to any disclaimer, the term of this patent is extended or adjusted under 35 U.S.C. 154(b) by 389 days.

(21) Appl. No.: 12/722,616

(22) Filed: Mar. 12, 2010

(65) Prior Publication Data

US 2011/0223219 A1 Sep. 15, 2011

(51) Int. Cl.
*A61K 31/00* (2006.01)

(52) U.S. Cl.
USPC .................................... 424/78.03; 424/400

(58) Field of Classification Search
None
See application file for complete search history.

(56) References Cited

U.S. PATENT DOCUMENTS

| | | | |
|---|---|---|---|
| 3,215,724 A | 11/1965 | Strobel et al. | |
| 3,439,088 A | 4/1969 | Edman | |
| 3,781,417 A | 12/1973 | Welters et al. | |
| 3,818,105 A | 6/1974 | Coopersmith et al. | |
| 4,970,252 A | 11/1990 | Sakuta et al. | |
| 5,236,986 A | 8/1993 | Sakuta | |
| 5,412,004 A | 5/1995 | Tachibana et al. | |
| 5,654,362 A | 8/1997 | Schulz, Jr. et al. | |
| 5,760,116 A | 6/1998 | Kilgour et al. | |
| 5,766,577 A * | 6/1998 | Hechavarria ................... | 424/63 |
| 5,811,487 A | 9/1998 | Schulz, Jr. et al. | |
| 5,837,793 A | 11/1998 | Harashima et al. | |
| 7,510,734 B2 | 3/2009 | Sullivan et al. | |
| 2002/0182237 A1 | 12/2002 | Bissett et al. | |
| 2004/0052759 A1 | 3/2004 | Sawaki et al. | |
| 2005/0142095 A1 * | 6/2005 | Scancarella et al. ............ | 424/74 |
| 2006/0034875 A1 | 2/2006 | Nakanishi et al. | |
| 2008/0031834 A1 | 2/2008 | Manelski et al. | |
| 2010/0323042 A1 * | 12/2010 | Collins et al. ................. | 424/735 |

FOREIGN PATENT DOCUMENTS

| | | |
|---|---|---|
| EP | 1097700 | 5/2001 |
| JP | 61018708 | 1/1986 |
| JP | 3127713 | 5/1991 |
| JP | 4356409 | 12/1992 |
| JP | 2002037739 | 2/2002 |
| JP | 2002037742 | 2/2002 |
| JP | 2003-081808 | 3/2003 |
| RO | 113114 | 4/1998 |
| WO | WO2004/024798 | 3/2004 |
| WO | WO2009/082511 | 7/2009 |
| WO | WO 2009082511 A1 * | 7/2009 |

OTHER PUBLICATIONS

Specification Sheet for JEEN International Corporation; Fairfiled, NJ 07004; JEESILC 35C; 5 pages; Jan. 2002.
Hedrick, James B.; MICA; Domestic Survey Data and Tables were prepared by: Linder Roberts; MICA; pp. 51.1-51.4 (4 pgs.); Tables 1-14 (7 pgs.); 1999.
http://www.gnpd.com; Mintel GNPD; Face Sculptor Make-Up Foundation; Record ID: 84210; Helena Rubinstein; Helena Rubinstein; Colour Cosmetics; Face Colour Cosmetics—Foundations/Fluid Illuminators; Turkey; Jan. 2001.
http://www.gnpd.com; Mintel GNPD; Lip Sculptor Treatment; Record ID: 81067; Helena Rubinstein; Helena Rubinstein; Skincare; Lip Care; France; Mar. 2001.
http://www.gnpd.com; Mintel GNPD; Skin Conditioning Makeup; Record ID: 838664; Revlon; Almay Truly Lasting Color; Colour Cosmetics; Face Colour Cosmetics—Foundations/Fluid Illuminators; Canada; Jan. 2008.
http://www.gnpd.com; Mintel GNPD; Comfort on Call Allergy Tested Relief Cream; Record ID: 1036835; Clinique; Clinique; Skincare; Face/Neck Care; UK; Jan. 2009.
http://www.gnpd.com; Mintel GNPD; Loose Powder; Record ID: 722455; Revlon; Revlon Colorstay; Colour Cosmetics; Face Colour Cosmetics—Powder; Japan; Jun. 2007.
http://www.gnpd.com; Mintel GNPD; Makeup With SoftFlex; Record ID: 632422; Revlon, Revlon Color Stay; Colour Cosmetics; Face Colour Cosmetics—Foundations/Fluid Iluminators; Australia; Dec. 2006.
http://www.gnpd.com; Mintel GNPD; Makeup with SoftFlex SPF 6 Combination/Oily Skin; Record ID: 722704, Revlon; Revlon Colorstay; Colour Cosmetics; Face Colour Cosmetics—Foundations/Fluid Illuminators; France; Jun. 2007.
http://www.gnpd.com; Mintel GNPD; Mousse Makeup; Record ID: 1111061; Revlon; Revlon Colorstay Mineral; Colour Cosmetics; Face Colour Cosmetics—Foundations/Fluid Illuminators; USA; May 2009.
http://www.gnpd.com; Mintel GNPD; Pressed Powder with SoftFlex; Record ID: 637565; Revlon; Revlon Colorstay; Colour Cosmetics; Face Colour Cosmetics—Powder; Venezuela; Jan. 2007.
PCT International Search Report; International Application No. PCT/US2011/027039; Completion Date: Nov. 28, 2011; Date of Mailing: Nov. 30, 2011.
PCT Written Opinion of the International Searching Authority, or the Declaration; International Application No. PCT/US2011/027039; Completion Date: Nov. 28, 2011; Date of Mailing: Nov. 30, 2011.

\* cited by examiner

*Primary Examiner* — Anand Desai
*Assistant Examiner* — Melissa Mercier
(74) *Attorney, Agent, or Firm* — Julie M. Blackburn

(57) ABSTRACT

A probiotic color cosmetic composition comprising at least one extract from a probiotic microorganism; at least one non-clay lamellar phyllosilicate mineral particulate; and at least one anti-inflammatory ingredient present in an amount sufficient to inhibit one or more of the pathways that contribute to skin inflammation; and a method for treating skin for improvement by applying to skin in need of such improvement the composition of the invention.

10 Claims, No Drawings

PROBIOTIC COLOR COSMETIC COMPOSITIONS AND METHODS

TECHNICAL FIELD

The invention is in the field of color cosmetic compositions with probiotic ingredients.

BACKGROUND OF THE INVENTION

The term "probiotic" refers to microorganisms that are believed to be healthy for the host organism. Examples of probiotic microorganisms include many types of lactic acid bacteria, e.g. bacteria that produce lactic acid as a metabolite, such as those belonging to the Order *Lactobacillales* or yeasts from the family *Saccharomyces*. Probiotic microorganisms are believed to provide many advantages when used in topical compositions. For example, according to U.S. Pat. No. 7,510,734, hereby incorporated by reference in its entirety, certain *lactobacillus* extracts have properties in stimulating beta-defensins, which have antibiotic activity against pathogens that come into contact with skin. Other types of extracts from probiotic microorganisms are known to have beneficial properties on skin such as free radical scavenging properties, anti-oxidant capability, and so on. It is known to use these types of extracts in skin care products. However, because color cosmetics such as foundation, blush, lipstick and so on are widely used by women, they represent another vehicle into which skin beneficial ingredients may be incorporated so that skin may receive nutrients from as many topical sources as possible.

However, color cosmetics are often more difficult to formulate. Color cosmetics such as foundations are often in emulsion form. Colored emulsions can have stability issues for a variety of reasons. For example, the pigments necessary to provide color are often bear positive or negative charges. That alone makes formulation of pigmented emulsions more difficult. The surfactant systems must be properly selected so that they are compatible with the other ingredients present, and the ionic charges of the colorants taken into consideration. In short, every ingredient incorporated into a pigmented emulsion composition has the potential to exert an effect on a system where stability is tricky at best.

Anhydrous color cosmetics are not free from their stability issues. If the compatibility of the oils, structuring agents and pigments used in these products are not properly considered these compositions can separate, discolor, or be otherwise commercially acceptable.

Accordingly, addition of probiotic ingredients into color cosmetics is fraught with difficulties in providing a cosmetic product that is stable, color true, and otherwise commercially acceptable.

SUMMARY OF THE INVENTION

The invention comprises color cosmetic compositions containing at least one probiotic microorganism extract; at least one lamellar mineral particulate; and at least one naturally occurring anti-inflammatory ingredient operable to inhibit one or more of the pathways that contribute to skin inflammation.

The invention is further directed to a method for treating skin for improvement comprising applying to skin in need if such improvement a color cosmetic composition comprising at least one probiotic microorganism extract; at least one lamellar mineral particulate; and at least one naturally occurring anti-inflammatory ingredient present in the composition in an amount sufficient to inhibit one or more of the pathways that contribute to skin inflammation.

DETAILED DESCRIPTION

I. Definitions

"Adhesion Pathway" is the pathway by which cells adhere to blood vessels and other skin tissues when injury or immune challenge has occurred.

"Chemotaxis Pathway" means the pathway where chemical signals cause inflammatory cells to migrate toward the site in the body, such as skin or tissue, where immune challenge has occurred. If such inflammatory cells are prevented from migrating to the site of immune challenge the resulting damage that such cells provide to skin or tissues can be mitigated.

"Collagenase Pathway" means the pathway by which the enzyme collagenase breaks down the peptide bonds in collagen and destroys extracellular structures such as those found in bacteria or infiltrating lymphocytes at the sites of inflammation. The collagenases released will cause tissue damage by breaking down collagen fibrils in the extra cellular matrix.

"COX Pathway" means the pathway by which the cyclooxygenase (COX) enzyme (including but not limited to cyclooxygenase-2 or COX-2) converts arachidonic acid and/or other fatty acids to prostaglandin or prostanoids which ultimately contributes to inflammation or pain in immune challenged tissue such as skin.

"Elastase Pathway" means the pathway by which the enzyme elastase degrades proteins including elastin that are found in bacteria and other molecules. When the Elastase Pathway is triggered the cascade of reactions contributes to inflammation or pain in immune challenged tissue such as skin. Elastase, a peptidase released from infiltrating neutrophils at the site of inflammation, will break down elastin, an elastic fiber that, together with collagen, helps determine the mechanical properties of skin and other tissues. Inhibition of elastase will minimize the damage that may be caused by infiltrating neutrophils which in turn will help preserve the integrity of the extra cellular matrix.

"Histamine Pathway" means the pathway where the amino acid histidine is decarboxylated to form histamine in response to immune challenge or other injury to tissue or skin. Histamine is a biogenic amine that is synthesized and stored in mast cells which reside primarily in the skin. Histamine plays a major role in the initiation of the inflammatory cascade. Upon stimulation, mast cells (and basophils) will release their stored histamine which will bind to H1 receptors on a variety of cells (including smooth muscle cells and endothelial cells in blood vessels) exerting its biologic effects. These effects include vasodilation, separation of endothelial cells (causing abnormal vascular permeability), pain and itching. Inhibition of histamine release provides amelioration from many of the adverse effects of inflammation.

"Histamine Receptor Pathway" means that pathway by which cellular receptors for histamine are activated to bind to histamine, which in turn contributes to the inflammatory condition of tissues or skin.

"Immune challenged" means tissues or skin subjected to environmental, bacterial or viral assaults and where any one or more of the Pathways that contribute to inflammation have been triggered.

"Inflammation" means, when used to describe skin, that the skin has been subjected to moderate to severe environmental or chemical assault and is moderately to severely immune challenged. Examples of inflammation include sunburn, windburn, acne, insect bites, cuts, burns, rosacea, and the like. Inflammation typically produces one or more of redness, pain, and heat in the skin.

"Inhibitor" means, when used with a particular Pathway, an ingredient or combination of ingredients that inhibits the Pathway in whole or in part. For example, Histamine Pathway Inhibitor means an ingredient or combination of ingredients that inhibits the Histamine Pathway in whole or in part.

"Irritation", when used to describe skin, means that the skin has been aggravated by environmental assaults or toxins, or application of products containing one or more ingredients to which the skin is sensitized or otherwise incompatible. Irritation may result in redness, itchiness, dryness, blemishes, enlarged pores, and so on. Irritated skin may also exhibit one or more of redness, pain, and heat.

"LO Pathway" means the pathway by which the enzyme lipooxygenase, preferably 5-lipooxygenase, catalyzes the conversion of arachidonic acid to 5-hydroperoxyeicosatetraenoic acid and then to leukotriene A4, which ultimately contributes to inflammation or pain in immune challenged tissue such as skin.

"Liquid" means a composition that is a pourable liquid at room temperature.

"Naturally occurring" means, with respect to the anti-inflammatory ingredient, that it is derived from natural sources and is not synthetic.

"Non-volatile" means that the ingredient has a vapor pressure of less than about 2 mm. of mercury at 20° C.

"Normal" or "Normalized", when used to describe skin, means skin that is in its optimum state of natural health. Normalizing skin can include treating skin to improve irritation or inflammation, or ameliorate or relieve conditions such as dark under eye circles, or to improve the appearance of wrinkles, lines, uneven pigmentation, sallowness, dryness, laxity, mottled skin, age spots, and the like.

"Pathway", when used with respect to inflammation, means a cascade of reactions that occurs when skin or tissue is exposed to immune challenge, and which ultimately contributes to skin inflammation.

"PDE Pathway" means that pathway by which PDE (phosphodiesterase) including phosphodiesterase-4 (PDE4) cleaves the phosphodiester bond that may be found in proteins and other molecules present in bacteria, viruses, and other molecules that contribute to skin inflammation. PDE4, in particular, is a member of a family of enzymes that catalyze the degradation of cAMP to the corresponding 5'-nucleotide monophosphate. PDE4 is abundant and is the major regulator of cAMP metabolism in almost every pro-inflammatory and immune cell. PDE4 inhibitors exert their anti-inflammatory effects by inhibiting the breakdown of cAMP (leading to an increased concentration of cAMP in immune cells) which will ultimately lead to a decrease in the production and release of pro-inflammatory cytokines such as Interleukin 1-β (IL-1β) and Tumor Necrosis Factor α (TNFα).

Percentages mentioned herein shall mean percentage by weight unless otherwise indicated.

"PLA-2 Pathway" means the pathway by which the phospholipase A2 (PLA-2) enzyme hydrolyzes phospholipids to form fatty acid lysophospholipid products such as arachidonic acid, which ultimately converts to leukotrienes and prostaglandins, which contribute to the inflammatory response in immune challenged tissue such as skin.

"Plurality" means more than one.

The term "probiotic microorganism" means bacteria belonging to the order *Lactobacillales*, including but not limited to those from the genus *Lactobacillus, Leuconostoc, Pediococcus, Lactococcus, Enterococcus, Oenococcus, Sporolactobacillus, Teragenococcus*, and so on; or a yeast belonging to the order *Saccharomyces*.

"Semi-solid" means a composition that exists in a cream or paste and which is neither pourable nor solid at room temperature.

"Solid" means a composition that is a solid at room temperature (e.g. 25° C.).

"Treating skin for improvement" means that the composition applied will reduce skin irritation, inflammation, or will be effective to normalize skin.

"VEGF Pathway" means the pathway by which VEGF (vascular endothelial growth factor) causes angiogensis (the formation of blood vessels) in immune challenged skin. In addition to inducing angiogenesis, VEGF also is responsible for increasing vascular leakage which will lead to increased edema in damaged tissue or skin.

"Volatile" means that the ingredient has a vapor pressure of about 2 mm. of mercury or greater at 20° C.

II. The Probiotic Microorganism Extract

The probiotic microorganism extract may be obtained from the fermentation of any probiotic bacteria or yeast including those from the order *Lactobacillales* or the genus *Saccharomyces* respectively. More preferred bacteria from the *Lactobacillales* order include the lactic acid producing bacteria from genuses such as *Abiotrophia, Aerococcus, Camobacterium, Enterococcus, Lactobacillus, Lactococcus, Leuconostoc, Oenococcus, Pediococcus, Sporolactobacillus, Teragenococcus*, and so on. Particularly desirable are bacteria from the *Lactobacillus* genus, of which there are a considerable number of species. Most preferred are *Lactobacillus Plantarum* or *Lactobacillus casei* or *rhamnosus*.

Suitable probiotic yeasts include those from the genus *Saccharomyces*, including species such as *Saccharomyces cerevisiae. boulardii, bulderi*, and so on.

In one preferred embodiment of the invention the probiotic microorganism extract used in the color cosmetic composition is obtained as set forth in U.S. Pat. No. 7,510,734 which is hereby incorporated by reference in its entirety, and has the CTFA name *Lactobacillus ferment*, which is defined as an extract obtained from the fermentation of *Lactobacillus*. Commercial sources include those sold under the trade names AC Probiotic 1 by Active Concepts LLC or *Lactobacillus Crispatus* KLB 46 sold by Natural F&P Co., Ltd of Korea. Also suitable are various derivatives including one having the CTFA name *Lactobacillus Ferment* Filtrate, which is a filtrate of the extract from *Lactobacillus Ferment*, which may be purchased from Active Concepts LLC as a mixture of salicylic acid and the filtrate sold under the trade name ACB Salicylic Acid Bioferment. Also suitable are derivatives having the CTFA names *Lactobacillus Ferment* Lysate which is a lysate of the extract from fermentation of *Lactobacillus*, or *Lactobacillus Ferment* Lysate Filtrate where the lysate of the extract from fermentation of *Lactobacillus* is filtered.

Also suitable are extracts from yeast such as *Saccharomyces* which are fermented alone or in combination with various plant materials, for example, apple, *ginseng*, garlic, and so on. Such ingredients have the CTFA names *Saccharomyces Ferment, Saccharomyces Ferment* Lysate, *Saccharomyces Ferment* Lysate Filtrate, *Saccharomyces*/grape *ferment, Saccharomyces/Lamanaria Saccharina ferment*, and so on; as well as extracts obtained from fermentation of *Saccharomyces* in combination with metals such as copper, calcium, magnesium, tourmaline, and so on.

Suitable ranges of the probiotic microorganism or *ferment* or lysate thereof may be from about 0.0001 to 35%, preferably from about 0.001 to 20%, more preferably from about 0.01 to 10%.

III. The Lamellar Mineral Particulate

The composition of the invention also contains at least one non-clay phyllosilicate lamellar mineral particulate. Suggested ranges may be from about 0.001 to 90%, preferably from about 0.01 to 80%, more preferably from about 0.1 to 75%. The lamellar phyllosilicate material preferably has a pH value ranging from about 5 to 9.5.

Most preferred are phyllosilicate minerals from the mica group, including biotite, muscovite, phlogopite, lepidolite, margarite, or glauconite.

The phyllosilicate mineral has a plate or sheet like configuration, and may have a particle size ranging from about 0.5 to 50 microns, preferably from about 1 to 45 microns. More preferred is where the phyllosilicate mineral has a pH value ranging from 5 to 11, preferably from 6 to 10, more preferably from 6 to 9. The term "pH value" means that a 4% aqueous suspension of the phyllosilicate material will have a pH within this range.

Most preferred is where the lamellar mineral particulate is mica.

The composition may optionally contain, in addition to the non-clay phyllosilicate lamellar mineral particulate, one or more clay based phyllosilicate minerals. The term "non-clay" means that the phyllosilicate minerals used in the composition do not come from the clay group, which are halloysite, kaolinite, illite, montmorillonite, vermiculite, talc, palygorskite, pyrophyllite. Conversely, clay based phyllosilicate minerals come from the clay group as identified above.

IV. The Anti-Inflammatory Ingredient

The composition contains one or more anti-inflammatory ingredients that are operable to inhibit one or more of the pathways that contribute to skin inflammation, e.g. Adhesion, Chemotaxis, Collagenase, COX, Elastase, Histamine, Histamine Receptor, LO, PDE, PLA-2, or VEGF. These pathways and the tests for confirming whether an ingredient will inhibit such pathway are set forth in PCT/WO2009/082511, assigned to ELC Management LLC, entitled Methods and Compositions for Treating Skin, naming inventors Donald Collins, Daniel Maes, and Neelam Muizzuddin, which is hereby incorporated by reference in its entirety.

Examples of anti-inflammatory ingredients that inhibit one or more of these pathways include, but are not limited to, those from the *Magnolia, Citrus, Camellia, Beta,* or *Mangifera* genuses. These extracts may be obtained by standard extraction methods from the seeds, pericarp, leaves, roots, stems, or other portions of the plant. The ant-inflammatory ingredients may range from about 0.0001-20%, preferably from about 0.0005-15%, more preferably from about 0.001-10% of one or more of the anti-inflammatory ingredients.

Other examples of anti-inflammatory ingredients include, but are not limited to, so on, including yeast *ferment* extract, *Padina Pavonica* extract, *thermus thermophilis ferment* extract, *Camelina Sativa* seed oil, *Boswellia Serrata* extract, *Olea Europa* extract, *Aribodopsis Thaliana* extract, *Acacia Dealbata* extract, *Acer Saccharinum* (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis; Salvia Sclarea, Rosmarinus Officianalis, Citrus Medica Limonum, Citrus Grandis* (grapefruit) peel extract, *Magnolia Grandiflora* bark extract, *Panax Ginseng, Poria Cocos* extract, *Siegesbeckia Orientalis, Fructus Mume, Ascophyllum Nodosum, Bifida Ferment* lysate, *Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus,* Hordeum Vulgare, *Cucumis Sativus, Evernia Prunastri, Evernia Furfuracea,* and mixtures thereof. C-A3

V. The Composition

The color cosmetic compositions may be in the form of aqueous gels or dispersions, emulsions, or anhydrous compositions and will generally be suitable for applying color to skin, hair, or lashes. Suitable aqueous gels contain from about 0.1 to 99% water from about 1-99.9% of other cosmetic ingredients. Emulsions may be in the oil in water or water in oil form, and generally comprise from about 0.1 to 99% water and from about 0.1 to 99% oil. Anhydrous compositions generally contain less than about 1% water, in addition to 0.1 to 90% oils, and optionally other ingredients. Such compositions may contain one or more of the following ingredients.

A. Oils

Suitable oils include silicones, esters, vegetable oils, synthetic oils, including but not limited to those set forth herein. Suggested amounts are from about 0.1 to 99%, preferably from about 0.5 to 95%, more preferably from about 1 to 80%. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C.

1. Volatile Oils

Suitable volatile oils generally have a viscosity ranging from about 0.5 to 5 centistokes 25° C. and include linear or cyclic silicones, paraffinic hydrocarbons, or mixtures thereof.

(a). Volatile Silicones

Cyclic silicones are one type of volatile silicone that may be used in the composition, including those having the following formula:

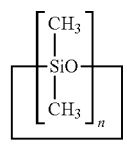

where n=3-6, preferably 4, 5, or 6. Preferred is where n=5 or 6, with such silicones having the CTFA names cyclopentasiloxane or cyclohexasiloxane.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, ethyl trimethicone, propyl trimethicone, butyl trimethicone and the like. Methyl trimethicone may be purchased from Shin-Etsu Silicones and has the trade name TMF 1.5, having the viscosity of 1.5 centistokes at 25° C. Such silicones have the general formula:

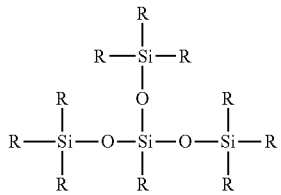

wherein each R is independently a $C_{1-4}$ alkyl, preferably methyl.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

2. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centistokes at 25° C. Examples of nonvolatile oils include, but are not limited to:

(a). Esters

Suitable esters are mono-, di-, and triesters. The composition may comprise one or more esters selected from the group, or mixtures thereof.

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

Suitable diesters are the reaction product of a dicarboxylic acid and an aliphatic or aromatic alcohol, or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may also be in the dimer or trimer form. Examples of diester oils that may be used in the compositions of the invention include those having a lower viscosity, e.g. diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Suitable triesters comprise the reaction product of a tricarboxylic acid and an aliphatic or aromatic alcohol, or alternatively, the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12\text{-}13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

(b). Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24\text{-}28}$ olefins, $C_{30\text{-}45}$ olefins, $C_{20\text{-}40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

(c). Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10\text{-}18}$ triglycerides, caprylic/capric/triglycerides, sweet almond oil, apricot kernel oil, sesame oil, *camelina sativa* oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

(d). Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C.

For example, such nonvolatile silicones may have the following general formula:

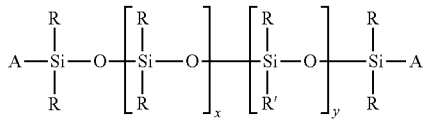

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit.

Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

B. Humectants

The compositions of the invention may also contain one or more humectants. If present, suggested ranges are from about 0.001 to 50%, preferably from about 0.01 to 45%, more preferably from about 0.05 to 40% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, trehalose, and so on. Also suitable is urea or sugar derivatives, e.g. ethylhexylglycerin. In one preferred embodiment, the humectants used in the composition of the invention are $C_{1-6}$, preferably $C_{2-4}$ alkylene glycols, most particularly butylene glycol.

C. Surfactants

If desired, the compositions of the invention may contain one or more surfactants. This is particularly desirable when the composition is in the form of an aqueous gel or emulsion. If present, the surfactant may range from about 0.001 to 50%, preferably from about 0.005 to 40%, more preferably from about 0.01 to 35% by weight of the total composition. Suitable surfactants may be silicone or organic, nonionic, anionic, amphoteric or zwitterionic. Such surfactants include, but are not limited to, those set forth herein.

1. Silicone Surfactants

Suitable silicone surfactants include polyorganosiloxane polymers that have amphiphilic properties, for example contain hydrophilic radicals and lipophilic radicals. These silicone surfactants may be liquids or solids at room temperature.

(a). Dimethicone Copolyols or Alkyl Dimethicone Copolyols

One type of silicone surfactant that may be used is generically referred to as dimethicone copolyol or alkyl dimethicone copolyol. It may be either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

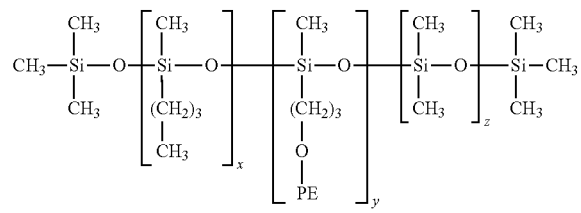

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename 5225C Formulation Aid, having the CTFA name cyclopentasiloxane (and) PEG/PPG-18/18 dimethicone; or Dow Coming 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name 'PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

(b). Crosslinked Silicone Surfactants

Crosslinked silicone surfactants, often referred to as emulsifying elastomers are suitable. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organopolysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. Nos. 5,412,004, 5,837,793 and 5,811,487, the contents of which are incorporated by reference. Polyoxyalkylenated silicone elastomers that may be used include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also surfactancy properties.

2. Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, Laureth 2-100, formed by the reaction of lauryl alcohol and ethylene oxide where the number of repeating ethylene oxide units is 2 to 100, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000. Also suitable are ethoxylated propoxylated derivatives of C6-30 saturated or unsaturated fatty acids, for example, Di-PPG-2 myreth-10 adipate, Di-PPG-2 Ceteth-4 adipate, Di-PPG Myristyl Ether Adipate, Other nonionic surfactants that may be used are formed by the reaction of a carboxylic acid with an alkylene oxide or with a polymeric ether or monomeric, homopolymeric, or block copolymeric ethers; or alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

D. Structuring Agents

It may also be desirable to include one or more structuring agents in the composition. Structuring agents will increase the viscosity, hence structure, the composition. Structuring agents may be lipophilic or hydrophilic, and form part of the aqueous or non-aqueous phase of the composition. If present, the structuring agent may range from about 0.1 to 60%, preferably from about 0.5 to 50%, more preferably from about 1 to 45% of the composition.

Desirable structuring agents include silicone elastomers, silicone gums or waxes, natural or synthetic waxes, polyamides, silicone polyamides and the like.

1. Silicone Elastomers

Silicone elastomers include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or a network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

2. Silicone Gums

Silicone gums are also suitable structuring agents. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million. Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

E. Sunscreens

It may also be desirable to include one or more sunscreens in the compositions of the invention. Such sunscreens include chemical UVA or UVB sunscreens or physical sunscreens in the particulate form.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula

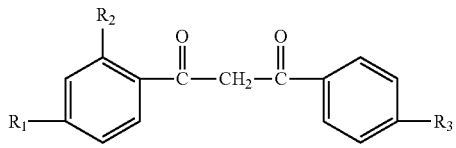

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl. Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

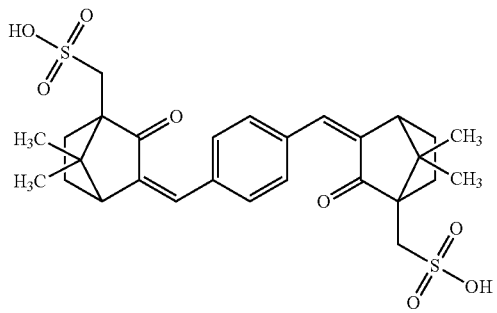 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 10% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

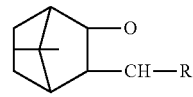

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

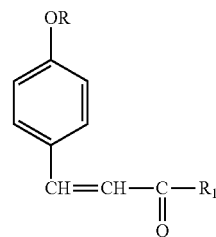

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

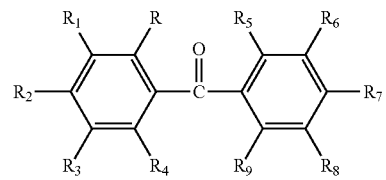

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

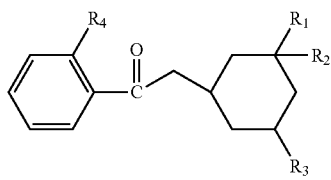

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

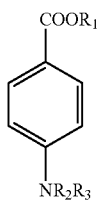

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl.

Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the gendal formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-100, preferably about from about 10 to 75 with ratios of UVA and UVB ranging from 1-3:1.

F. Film Formers

It may be desired to incorporate one or more film formers into the compositions of the invention. Film formers will generally enhance the film formed by the cosmetic applied to the skin and, in some cases, promote water resistance or transfer resistance. If present, such film formers may range from about 0.1 to 50%, preferably from about 0.5 to 40%, more preferably from about 1 to 35% by weight of the total composition.

Suitable film formers may be based on silicone or organic polymers. Particularly preferred are crosslinked silicone resins generally referred to as MT or MQ resins. Examples of such resins include the MQ resin trimethylsiloxysilicate or an MT resin called polymethylsilsesquioxane. Trimethylsiloxysilicate may be purchased from Dow Corning under the tradename 749 Fluid which is about a 50/50 mixture of trimethylsiloxysilicate and cyclomethicone, or General Electric under the tradename SR1000. Polymethylsilsesquioxane may be purchased from Wacker-Chemie under the tradename MK resin or Momentive.

The composition may contain other ingredients including preservatives, botanical extracts, vitamins, antioxidants, and the like.

VI. Particulate Materials

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

A. Powders

The particulate matter may be colored or non-colored (for example white) non-pigmented powders. Suitable non-pigmented powders include bismuth oxychloride, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, titanium dioxide, zinc laurate, zinc myristate, zinc rosinate, alumina, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

B. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

VII. Preservatives

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition is free of parabens.

VIII. Vitamins and Antioxidants

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are retinyl palmitate, retinol. retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

IX. The Cosmetic Compositions

Typical color cosmetic compositions that are in emulsion form such as foundations will preferably contain from about 5-98% water, 1-85% oil, and from about 0.1 to 20% of one or more surfactants in addition to from about 0.0001 to 35% of the probiotic microorganism extract, and from about 0.001 to 90% of the lamellar mineral particulate, and from about 0.1 to 65% of particulates that are pigments or a combination of pigments and powders.

Typical anhydrous color cosmetic composition such as blush, eyeshadow, eyeliner, lipstick, and so one preferably contain from about 1-95% oil, from about 0.0001 to 35% of the probiotic microorganism extract, and from about 0.001 to 90% of the lamellar mineral particulate, and from about 0.1 to 65% of particulates that are pigments or a combination of pigments and powders.

Typical mascara compositions generally contain from about 5-98% water, 1-85% oil, and from about 0.1 to 20% surfactant in addition to natural or synthetic polymers that are film forming, such as aqueous dispersions of acrylic copolymers, aqueous dispersions of polyurethane, or silicone resins, from about 0.0001 to 35% of the probiotic microorganism extract, and from about 0.001 to 90% of the lamellar mineral particulate, and from about 0.1 to 65% of particulates that are pigments or a combination of pigments and powders.

Examples of preferred compositions include but are not limited to the following:

A pigmented emulsion foundation makeup composition comprising volatile silicone, at least one sunscreen, at least one non-volatile silicone, at least one linear silicone surfactant, at least one crosslinked silicone surfactant, at least one probiotic microorganism extract, at least one lamellar mineral particulate; and at least one anti-inflammatory ingredient. Preferred is where the volatile silicone is a branched volatile silicone, the sunscreen comprises at least one UVB sunscreen, the non-volatile silicone is dimethicone or phenyl trimethicone, the linear silicone surfactant is dimethicone copolyol, the crosslinked silicone surfactant is an emulsifying siloxane elastomer, and the probiotic microorganism extract is from *Lactobacillus* and the lamellar particulate comprises mica. Even more preferred is where the branched volatile silicone is methyl trimethicone and the crosslinked silicone surfactant is dimethicone/PEG-10/15 crosspolymer; with all percentage ranges for such ingredients as set forth above.

An anhydrous pigmented composition in the pressed or loose powder containing the probiotic microorganism extract, at least one anti-inflammatory ingredient, and a mixture of powders and pigments, and at least one oil. Preferred is where the probiotic microorganism extract is incorporated into the composition by spray drying the particulates incorporated into the composition.

The invention will be described in connection with the following examples which are set forth for purposes of illustration only.

EXAMPLE 1

An emulsion foundation makeup composition in accordance with the invention was prepared as follows:

| Ingredient | % by weight |
| --- | --- |
| Deionized water | QS100 |
| Titanium dioxide/methicone | 9.34 |
| Methyl trimethicone | 8.75 |
| Ethylhexylmethoxycinnamate | 6.00 |
| Phenyl trimethicone | 6.00 |
| Isopropyl titanium triisostearate/C12-15 alkyl benzoate/polyglyceryl-6 polyricinoleate/zinc oxide/caprylyl methicone | 6.00 |
| Triethylhexanoin | 5.00 |
| Titanium dioxide/aluminum hydroxide/sodium myristoyl sarcosinate/dimethicone | 5.00 |
| Butylene glycol | 4.40 |
| Dimethicone/dimethicone PEG-10/15 crosspolymer | 3.00 |
| Trimethylsiloxysilicate | 2.00 |
| Dimethicone/diemthicone crosspolymer-3 | 2.00 |
| Iron oxides/methicone | 1.68 |
| PEG-10 dimethicone | 1.50 |
| Lauryl PEG-9 polydimethylsiloxyethyl dimethicone | 1.50 |
| Glycerin | 1.00 |
| Sodium mannose phosphate | 1.00 |
| Mica/methicone | 1.00 |
| Bismuth oxychloride | 1.00 |
| Phenoxyethanol | 0.70 |
| Iron oxides/methicone | 0.68 |
| Sodium chloride | 0.60 |
| Tocopheryl acetate | 0.50 |
| Dimethicone | 0.50 |
| Iron oxides/methicone | 0.30 |
| Mica/titanium dioxide/iron oxides | 0.25 |
| Disteardimonium hectorite | 0.20 |
| *Astrocaryum murumuru* seed butter | 0.20 |
| Lecithin | 0.10 |
| *Citrus grandis* (grapefruit) peel extract | 0.10 |
| Caffeine | 0.10 |

-continued

| Ingredient | % by weight |
|---|---|
| Disodium EDTA | 0.05 |
| Laureth-7 | 0.05 |
| Water/polyaminopropyl biguanide | 0.05 |
| Magnolia Grandiflora bark extract | 0.05 |
| Poria Cocos extract | 0.05 |
| Lactobacillus ferment | 0.03 |

The composition was prepared by combining the water phase and oil phase ingredients and mixing well to emulsify. The resulting foundation makeup composition was a water in oil emulsion.

EXAMPLE 2

Pressed and loose powder compositions according to the invention were made as follows:

| Ingredient | Pressed Powder | Loose Powder |
|---|---|---|
| Mica/lauroyl lysine | 40.00 | 26.51 |
| Mica | QS100 | QS100 |
| Polyethylene |  | 10.00 |
| Zinc stearate | 5.20 |  |
| Bismuth oxychloride/silica/mica |  | 3.00 |
| Silica | 4.00 |  |
| Octyldodecyl stearoyl stearate | 3.70 |  |
| Isopropyl palmitate |  | 1.00 |
| Magnesium myristate | 2.00 | 1.00 |
| Titanium dioxide | 1.00 |  |
| Polyethylene | 1.00 |  |
| HDI/trimethylol hexyllactone crosspolymer/silica | 1.00 | 6.00 |
| Bentonite | 1.00 | 0.50 |
| Iron oxides | 0.52 |  |
| FD&C Yellow No. 5 Aluminum Lake | 0.34 | 0.39 |
| Sodium dehydroacetate | 0.30 |  |
| Lecithin | 0.20 | 0.10 |
| Squalane | 0.20 | 0.10 |
| Chlorphenesin | 0.20 | 0.30 |
| Astrocaryum Murumuru seed butter | 0.20 | 0.20 |
| Tocopheryl acetate | 0.10 | 0.10 |
| Caprylyl glycol | 0.10 |  |
| Citrus Grandis (grapefruit) peel extract | 0.10 | 0.10 |
| Caffeine | 0.10 | 0.10 |
| Poria Cocos extract | 0.05 | 0.05 |
| Magnolia Grandiflora bark extract | 0.05 | 0.05 |
| Potassium sorbate |  | 0.20 |
| Tetrasodium EDTA |  | 0.05 |
| Iron oxides | 0.532 | 0.25 |
| Lactobacillus ferment | 0.10 | 0.10 |

The compositions were prepared by spraying the *lactobacillus ferment* onto the particulates such as the mica, titanium dioxide, and the like, then formulating them into the powder compositions.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A probiotic color cosmetic composition in pigmented emulsion form comprising: (a) at least one extract from a fermented *Lactobacillus* probiotic microorganism; (b) at least one lamellar phyllosilicate mineral particulate from the mica group; (c) at least one anti-inflammatory ingredient from the *Citrus* genus; (d) at least one emulsifying siloxane elastomer; (e) at least one silicone resin; and (f) at least one linear silicone surfactant.

2. The composition of claim 1 wherenin the anti-inflammatory botanical extract from the *Citrus* genus is an inhibitor of one or more of the following pathways:
Adhesion, Chemotaxis, Collagenase, COX, Elastase, Histamine, Histamine Receptor, LO, PDE, PLA-2, or VEGF.

3. The composition of claim 2 wherein the anti-inflammatory botanical extract from the *Citrus* genus is an inhibitor of one or more of the Adhesion pathway, Chemotaxis pathway, Elastase Pathway, or Histamine Pathway.

4. A pigmented anhydrous powder composition comprising(a) an anti-inflammatory ingredient from the *Citrus* genus; (b) particulates comprising at least one lamellar phyllosilicate mineral particulate from the mica group; and a *Lactobacillus* probiotic microorganism extract spray dried onto particulates present in the composition prior to their incorporation into the composition.

5. A method for treating skin for improvement comprising applying to skin in need of improvement the color cosmetic composition according to claim 1.

6. The method of claim 5 wherein the composition is a foundation makeup, blush, eyeshadow, concealer, or lipstick.

7. The method of claim 6 wherein the composition is applied once per day.

8. The method of claim 5 wherein the improvement to be treated is irritation, inflammation, or normalization of skin.

9. A method for treating skin for improvement comprising applying to skin in need of improvement the color cosmetic composition according to claim 4.

10. The method of claim 9 wherein the color cosmetic composition is a foundation makeup or concealer.

* * * * *